United States Patent
Berry Ann et al.

(10) Patent No.: US 10,293,126 B2
(45) Date of Patent: May 21, 2019

(54) INSPIRATORY PRESSURE CONTROL IN VOLUME MODE VENTILATION

(71) Applicant: KONINKLIJKE PHILIPS N.V., Eindhoven (NL)

(72) Inventors: Nathan John Berry Ann, Pittsburgh, PA (US); William Anthony Truschel, Oakmont, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 633 days.

(21) Appl. No.: 14/652,579

(22) PCT Filed: Sep. 24, 2013

(86) PCT No.: PCT/IB2013/058788
§ 371 (c)(1),
(2) Date: Jun. 16, 2015

(87) PCT Pub. No.: WO2014/096996
PCT Pub. Date: Jun. 26, 2014

(65) Prior Publication Data
US 2015/0328419 A1   Nov. 19, 2015

Related U.S. Application Data

(60) Provisional application No. 61/738,665, filed on Dec. 18, 2012.

(51) Int. Cl.
*A61M 16/00* (2006.01)
*A61M 16/06* (2006.01)
(Continued)

(52) U.S. Cl.
CPC .... *A61M 16/0069* (2014.02); *A61M 16/0003* (2014.02); *A61M 16/024* (2017.08);
(Continued)

(58) Field of Classification Search
CPC .......... A61M 16/0003; A61M 16/0051; A61M 16/0066; A61M 16/0069; A61M 16/021;
(Continued)

(56) References Cited

U.S. PATENT DOCUMENTS 5,752,509 A * 5/1998 Lachmann .......... A61M 16/024
128/203.12
6,041,780 A * 3/2000 Richard ................ A61M 16/00
128/204.18
(Continued)

FOREIGN PATENT DOCUMENTS

CN      101035584 A    9/2007
CN      1022452424 A   11/2011
(Continued)

*Primary Examiner* — Jan Christopher Merene
*Assistant Examiner* — Joseph D Boecker
(74) *Attorney, Agent, or Firm* — Michael W. Haas

(57) ABSTRACT

The present disclosure pertains to a mechanical ventilator system configured to deliver a pressurized flow of breathable gas to the airway of a subject. The system is configured to generate the pressurized flow of breathable gas according to a volume control mode therapy regime that delivers a target tidal volume to the subject during inhalation. During an individual inhalation, the system is configured to determine and/or adjust an inspiratory pressure level of the pressurized flow of breathable gas of the volume control mode therapy regime. The inspiratory pressure level is adjusted such that during the inhalation the inspiratory pressure level is not reduced to impede respiratory effort by the subject responsive to the target tidal volume being exceeded during the inhalation. The system comprises one or more of a pressure generator, a subject interface, one or more sensors, one or more processors, a user interface, electronic storage, and/or other components.

12 Claims, 2 Drawing Sheets

(51) Int. Cl.
*A61M 16/20* (2006.01)
*A61M 16/16* (2006.01)

(52) U.S. Cl.
CPC .......... *A61M 16/06* (2013.01); *A61M 16/201* (2014.02); *A61M 16/161* (2014.02); *A61M 2016/003* (2013.01); *A61M 2016/0027* (2013.01); *A61M 2205/33* (2013.01); *A61M 2205/3331* (2013.01); *A61M 2205/3334* (2013.01); *A61M 2205/3365* (2013.01); *A61M 2205/3368* (2013.01); *A61M 2205/3375* (2013.01); *A61M 2205/50* (2013.01); *A61M 2205/502* (2013.01); *A61M 2205/505* (2013.01); *A61M 2205/52* (2013.01)

(58) Field of Classification Search
CPC .............. A61M 16/022; A61M 16/024; A61M 16/201; A61M 16/202; A61M 2016/0027; A61M 2016/003; A61M 2205/3331; A61M 2205/3334; A61M 2205/3344; A61M 2205/3365; A61M 2205/3375; A61M 2205/50; A61M 2205/502; A61M 2205/505; A61M 2205/52; A61M 16/00; A61M 16/0057; A61M 16/006; A61M 16/0072; A61B 5/085; A61B 5/087; A61B 5/091
See application file for complete search history.

(56) References Cited

U.S. PATENT DOCUMENTS

| | | | | |
|---|---|---|---|---|
| 6,390,091 B1 * | 5/2002 | Banner | ............. | A61M 16/0051 128/202.22 |
| 8,857,430 B2 | 10/2014 | Berthon-Jones | | |
| 9,775,558 B2 | 10/2017 | Truschel | | |
| 2003/0066528 A1 * | 4/2003 | Hill | ...................... | A61M 16/026 128/204.18 |
| 2006/0162727 A1 * | 7/2006 | Biondi | .................. | A61M 16/00 128/204.21 |
| 2006/0249150 A1 * | 11/2006 | Dietz | .................. | A61M 16/022 128/204.18 |
| 2007/0062529 A1 | 3/2007 | Choncholas | | |
| 2008/0066753 A1 | 3/2008 | Martin | | |
| 2008/0236582 A1 * | 10/2008 | Tehrani | .................. | A61H 31/02 128/204.22 |
| 2011/0017214 A1 * | 1/2011 | Tehrani | ............. | A61M 16/0051 128/204.22 |
| 2011/0197887 A1 * | 8/2011 | Truschel | ........... | A61M 16/0051 128/204.23 |
| 2011/0232644 A1 | 9/2011 | Doyle | | |
| 2012/0226444 A1 * | 9/2012 | Milne | ...................... | A61B 5/08 702/19 |
| 2012/0272960 A1 * | 11/2012 | Milne | .................. | A61M 16/00 128/204.23 |
| 2012/0298108 A1 | 11/2012 | Kane | | |
| 2013/0220324 A1 * | 8/2013 | Jafari | .................... | A61M 16/00 128/204.23 |
| 2013/0247914 A1 * | 9/2013 | Truschel | ........... | A61M 16/0051 128/204.23 |

FOREIGN PATENT DOCUMENTS

| | | |
|---|---|---|
| CN | 102451506 A | 5/2012 |
| CN | 102711889 A | 10/2012 |
| GB | 2472116 A | 1/2011 |
| JP | 2011005274 A | 1/2011 |
| WO | WO2009123981 A1 | 10/2009 |
| WO | WO2012024733 A2 | 3/2012 |
| WO | WO2012069957 A1 | 5/2012 |
| WO | WO2012085748 A1 | 6/2012 |
| WO | WO2012127358 A1 | 9/2012 |

\* cited by examiner

INSPIRATORY PRESSURE CONTROL IN VOLUME MODE VENTILATION

CROSS-REFERENCE TO RELATED APPLICATIONS

This patent application claims the priority benefit under 35 U.S.C. § 371 of international patent application no. PCT/IB2013/058788, filed Sep. 24, 2013, which claims the priority benefit under 35 U.S.C. § 119(e) of U.S. Provisional Application No. 61/738,665, filed on Dec. 18, 2012, the contents of which are herein incorporated by reference.

BACKGROUND OF THE INVENTION

1. Field of the Invention

The present disclosure pertains to a mechanical ventilator system configured to deliver a pressurized flow of breathable gas to the airway of a subject.

2. Description of the Related Art

A mechanical ventilator assists breathing by pushing air into a patient's lungs. Ventilators may operate under different control modes. One control mode is a volume control mode in which the ventilator delivers a prescribed volume of air to the patient. Operating in a volume control mode, a ventilator may reduce the pressure provided to the patent during inhalation toward zero or below, responsive to the patient exerting muscular effort during inhalation, in an effort to maintain a target volume and/or flow. The reduced pressure may counteract the effort of the patient during inhalation.

SUMMARY OF THE INVENTION

Accordingly, one or more aspects of the present disclosure relate to a mechanical ventilator system configured to deliver a pressurized flow of breathable gas to the airway of a subject. The mechanical ventilator system comprises a pressure generator, one or more sensors, a user interface, and one or more processors. The pressure generator is configured to generate the pressurized flow of breathable gas. The one or more sensors are configured to generate output signals conveying information related to one or more gas parameters of the pressurized flow of breathable gas. The user interface is configured to receive entry and/or selection of control inputs that select a target tidal volume. The one or more processors are configured to execute computer program modules. The computer program modules comprise a control module, a gas parameter module, an airway parameter module, and an inspiratory pressure module. The control module is configured to control operation of the pressure generator to generate the pressurized flow of breathable gas according to a volume control mode therapy regime that delivers the target tidal volume.

The gas parameter module is configured to determine one or more gas parameters of the pressurized flow of breathable gas based on the output signals, wherein the one or more gas parameters are determined multiple times per inhalation of the subject. The airway parameter module is configured to determine one or more airway parameters of the airway of the subject, wherein the one or more airway parameters are determined multiple times per inhalation of the subject. The inspiratory pressure module is configured to dynamically determine an inspiratory pressure level of the pressurized flow of breathable gas of the volume control mode therapy regime during an inhalation to achieve the target tidal volume, the determination based on the determined one or more airway parameters and the determined one or more gas parameters such that the inspiratory pressure level during the inhalation is not reduced to impede respiratory effort by the subject responsive to the target tidal volume being exceeded during the inhalation.

Yet another aspect of the present disclosure relates to a method to deliver a pressurized flow of breathable gas to the airway of a subject with a mechanical ventilator system. The mechanical ventilator system comprises a pressure generator, one or more sensors, a user interface, and one or more processors. The one or more processors are configured to execute computer program modules. The computer program modules comprise a control module, a gas parameter module, an airway parameter module, and an inspiratory pressure module. The method comprises generating the pressurized flow of breathable gas with the pressure generator; generating output signals conveying information related to one or more gas parameters of the pressurized flow of breathable gas with the one or more sensors; receiving entry and/or selection of control inputs that select a target tidal volume with the user interface; controlling operation of the pressure generator to generate the pressurized flow of breathable gas according to a volume control mode therapy regime that delivers the target tidal volume with the control module; determining one or more gas parameters of the pressurized flow of breathable gas based on the output signals with the gas parameter module, wherein the one or more gas parameters are determined multiple times per inhalation of the subject; determining one or more airway parameters of the airway of the subject with the airway parameter module, wherein the one or more airway parameters are determined multiple times per inhalation of the subject; and dynamically determining an inspiratory pressure level of the pressurized flow of breathable gas of the volume control mode therapy regime during an inhalation to achieve the target tidal volume, with the inspiratory pressure module, the determination based on the determined one or more airway parameters and the determined one or more gas parameters, such that the inspiratory pressure level during the inhalation is not reduced to impede respiratory effort by the subject responsive to the target tidal volume being exceeded during the inhalation.

Still another aspect of the present disclosure relates to a mechanical ventilator system configured to deliver a pressurized flow of breathable gas to the airway of a subject. The mechanical ventilator system comprising means for generating the pressurized flow of breathable gas; means for generating output signals conveying information related to one or more gas parameters of the pressurized flow of breathable gas; means for receiving entry and/or selection of control inputs that select a target tidal volume; and means for executing computer program modules. The computer program modules comprising means for controlling operation of the means for generating the pressurized flow of breathable gas to generate the pressurized flow of breathable gas according to a volume control mode therapy regime that delivers the target tidal volume; means for determining one or more gas parameters of the pressurized flow of breathable gas based on the output signals, wherein the one or more gas parameters are determined multiple times per inhalation of the subject; means for determining one or more airway parameters of the airway of the subject, wherein the one or more airway parameters are determined multiple times per inhalation of the subject; and means for dynamically determining an inspiratory pressure level of the pressurized flow of breathable gas of the volume control mode therapy regime during an inhalation to achieve the target tidal volume, the determination based on the determined one or more airway parameters and the determined one or more gas parameters such that the inspiratory pressure level during the inhalation is not reduced to impede respiratory effort by the subject responsive to the target tidal volume being exceeded during the inhalation.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
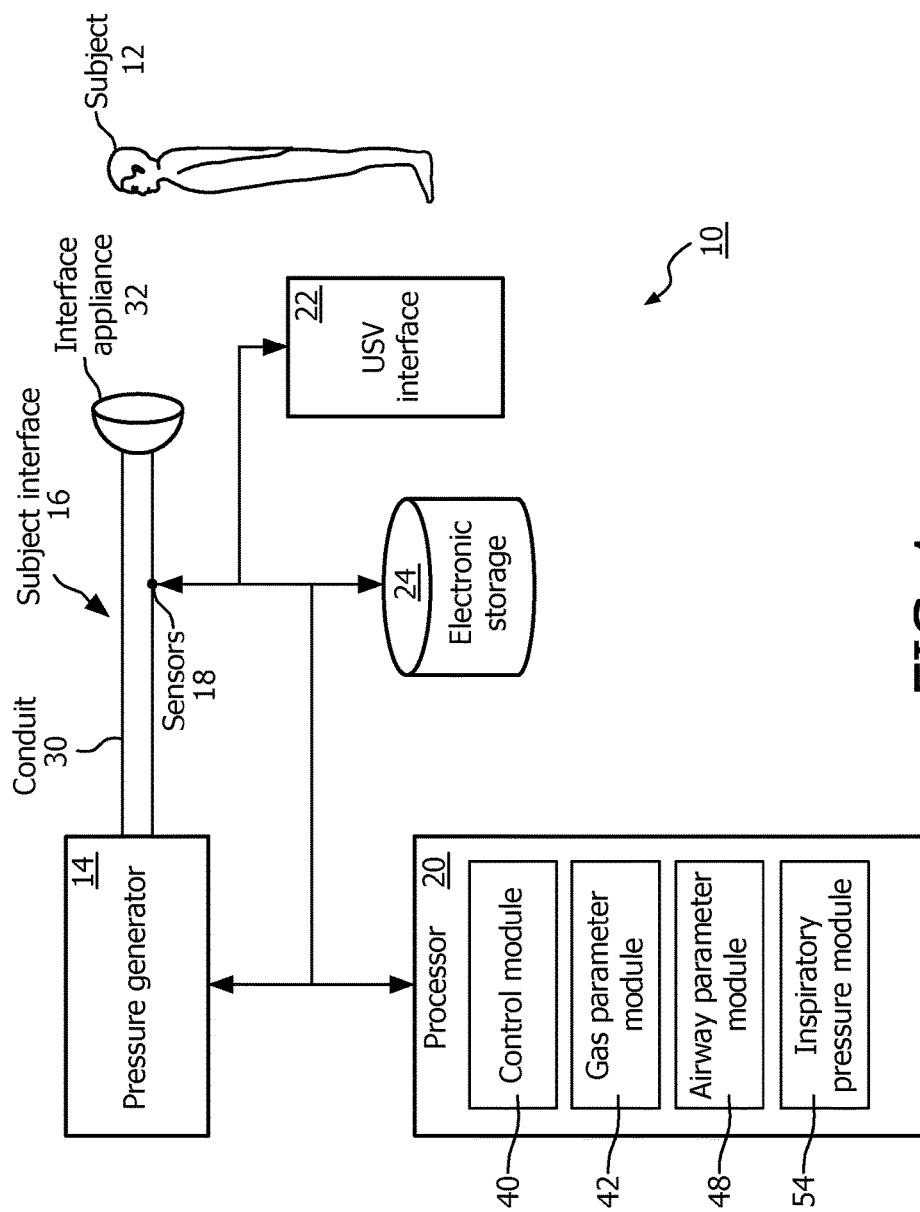
FIG. 1 is a schematic illustration of a mechanical ventilator system configured to deliver a pressurized flow of breathable gas to the airway of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a mechanical ventilator system 10 configured to deliver a pressurized flow of breathable gas to the airway of a subject 12. One or more parameters of the pressurized flow of breathable gas are controlled to mechanically ventilate subject 12. This may include providing mechanical ventilation to assist subject 12 as subject 12 attempts to breathe for himself. System 10 is configured to generate the pressurized flow of breathable gas according to a volume control mode therapy regime that delivers a target tidal volume to subject 12 during inhalation.

During an individual inhalation, system 10 is configured to adjust an inspiratory pressure level of the pressurized flow of breathable gas of the volume control mode therapy regime. The inspiratory pressure level is adjusted such that during the inhalation the inspiratory pressure level is not reduced to impede respiratory effort by subject 12 responsive to the target tidal volume being exceeded during the inhalation.

System 10 is configured to adjust the inspiratory pressure level based on one or more determined gas parameters, one or more determined airway parameters, an airway model, and/or other information. The airway model may comprise an algorithm configured to output a real time pressure set point level. The airway model may be utilized by system 10 to generate multiple real time pressure set point levels during the inhalation. Input variables to the model may include the one or more determined gas parameters, the one or more determined airway parameters, and/or other parameters. In some embodiments, system 10 comprises one or more of a pressure generator 14, a subject interface 16, one or more sensors 18, a processor 20, a user interface 22, electronic storage 24, and/or other components.

Pressure generator 14 is configured to generate a pressurized flow of breathable gas for delivery to the airway of subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the flow rate, the tidal volume, the pressure, and/or other parameters of the flow of gas to provide volume control mode pressure support and/or ventilation to the airway of subject 12. The volume control mode pressure support may at least partially mechanically ventilate subject 12 as subject 12 attempts to breathe along with the ventilation provided by system 10.

Pressure generator 14 receives a flow of gas from a gas source, such as the ambient atmosphere, and elevates and/or reduces the pressure of that gas for delivery to the airway of a patient. Pressure generator 14 is any device, such as, for example, a pump, blower, piston, or bellows, that is capable of elevating and/or reducing the pressure of the received gas for delivery to a patient. Pressure generator 14 may comprise one or more valves for controlling the pressure and/or flow of gas, for example. The present disclosure also contemplates controlling the operating speed of the blower, either alone or in combination with such valves, to control the pressure and/or flow of gas provided to the patient.

Subject interface 16 is configured to deliver the pressurized flow of breathable gas to the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit, that places interface appliance 32 in fluid communication with pressure generator 14. Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

Sensors 18 are configured to generate output signals conveying information related to one or more gas parameters of the pressurized flow of breathable gas. The one or more gas parameters may comprise one or more of a flow rate, a volume, a pressure, a composition (e.g., concentration(s) of one or more constituents), temperature, humidity, acceleration, velocity, acoustics, changes in a parameter indicative of respiratory effort by subject 12, and/or other gas parameters. Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters). Although sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, in communication with subject 12, and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program modules. The one or more computer program modules may comprise one or more of a control module 40, a gas parameter module 42, an airway parameter module 48, an inspiratory pressure module 54, and/or other modules. Processor 20 may be configured to execute modules 40, 42, 48, and/or 54 by software; hardware; firmware; some combination of software, hardware, and/or firmware; and/or other mechanisms for configuring processing capabilities on processor 20.

It should be appreciated that although modules 40, 42, 48, and 54 are illustrated in FIG. 1 as being co-located within a single processing unit, in implementations in which processor 20 comprises multiple processing units, one or more of modules 40, 42, 48, and/or 54 may be located remotely from the other modules. The description of the functionality provided by the different modules 40, 42, 48, and/or 54 described below is for illustrative purposes, and is not intended to be limiting, as any of modules 40, 42, 48, and/or 54 may provide more or less functionality than is described. For example, one or more of modules 40, 42, 48, and/or 54 may be eliminated, and some or all of its functionality may be provided by other modules 40, 42, 48, and/or 54. As another example, processor 20 may be configured to execute one or more additional modules that may perform some or all of the functionality attributed below to one of modules 40, 42, 48, and/or 54.

Control module 40 is configured to control pressure generator 14 to generate the flow of gas in accordance with a volume control mode pressure support therapy regime. Control module 40 is configured to control pressure generator 14 based on information related to the output signals from sensors 18, information determined by gas parameter module 42, information entered by a user to user interface 22, and/or other information. The pressurized flow of gas generated by the pressure generator is controlled to replace and/or compliment a patient's regular breathing. Airway ventilation therapy may be used to maintain an open airway in a patient so that oxygen and carbon dioxide may be exchanged more easily, requiring little and/or no effort from the patient. The volume control mode therapy regime is configured such that control module 40 causes pressure generator 14 to deliver a target tidal volume. Control module 40 is configured to cause pressure generator 14 to deliver the target tidal volume based on the output signals from sensors 18, control inputs entered and/or selected by a user via user interface 22 that select the target tidal volume, and/or other information.

In some embodiments, control module 40 may be configured to control pressure generator 14 to generate the flow of gas in accordance with a ventilation and/or positive airway pressure support therapy regime in addition to and/or instead of the volume control mode therapy regime. By way of non-limiting example, control module 40 may control pressure generator 14 such that the pressure support provided to the subject via the flow of gas comprises continuous positive airway pressure support (CPAP), bi-level positive airway pressure support (BPAP), proportional positive airway pressure support (PPAP), and/or other types of pressure support therapy.

Gas parameter module 42 is configured to determine one or more gas parameters of the pressurized flow of breathable gas. The one or more gas parameters are determined based on the output signals. The one or more gas parameters may be determined multiple times per inhalation of subject 12. One or more of the one or more gas parameters may be determined at regular time intervals (e.g., 10 ms) during an inhalation of subject 12. The one or more gas parameters may be determined one or more times for each individual inhalation in a series of inhalations. The information determined by gas parameter module 42 may be used for controlling pressure generator 14, stored in electronic storage 24, and/or used for other uses. In some embodiments, one or more determined parameters may be used by gas parameter module 42 to further determine additional parameters. For example, a current flow rate may be compared to a target flow rate to determine a flow rate error. The one or more gas parameters may be related to one or more of a flow rate, a volume, a pressure, and/or other parameters. For example, the one or more gas parameters may comprise a real time flow rate, a real time flow rate set point, a flow rate target, an inspired volume, a real time volume set point, a volume target, a volume set point, a flow error, a flow error difference, a flow error sum, an inspired volume error, and/or other parameters. In some embodiments, gas parameter module 42 may be configured to determine one or more gain scaling terms.

The real time flow rate may be an instantaneous flow rate of the pressurized flow of breathable gas determined by gas parameter module 42. The real time flow rate may be determined multiple times during an inhalation of subject 12.

The real time flow rate set point, $Q_N$, may be an instantaneous flow rate set point determined from a flow rate set point profile. The real time flow rate set point may have units of liters/second, for example. The real time flow rate set point may be determined multiple times per inhalation of subject 12. The flow rate set point profile, $Q_{SET}$, is generated based on a flow rate set point algorithm, and may be comprised of a set of $Q_N$ values. The volume set point, $V_{SET}$, may be an input to the flow rate set point algorithm. The flow rate set point profile may change from breath to breath of subject 12.

The flow rate target, $Q_{TARGET,N}$, may be an instantaneous flow rate target determined from a flow rate target profile, $Q_{TARGET}$, where N represents one or more time points during an inhalation of subject 12. The flow rate target profile represents an ideal flow rate waveform. The flow rate target profile may be determined based on the entries and/or selections made by subject 12 and/or other users to user interface 22.

The inspired volume, $V_{INSP}$, may be a volume of gas inspired by subject 12 during an inhalation. The inspired volume may be determined multiple times during the inhalation. Each determination of the inspired volume may include the total volume of gas inspired by the subject during the inhalation up to the time of determination.

The volume target, $V_{TARGET}$, may be an instantaneous target volume determined based on the entries and/or selections made by subject 12 and/or other users to user interface 22. The target volume may be determined multiple times per inhalation of subject 12.

The volume set point, $V_{SET}$, is determined by gas parameter module 42, based on the error, $V_e$, between the volume target, $V_{TARGET}$, and the inspired volume, $V_{INSP}$. For example, $V_{SET}$ may be determined by acting on the volume error using a Proportional (P), Integral (I), or combined (PI) control scheme, or some other servo mechanism. Bounds may be placed on the control action to prevent large corrections, or to maintain stable volume delivery.

The real time volume set point, $V_N$, is the result of a running integration of the flow rate set point profile throughout inhalation, to obtain a volume (e.g., in liters).

Modifications to the volume target from the user interface 22 can be applied directly to the volume set point to further increase response time to changes in the prescribed volume.

The flow error, $Q_{e,N}$, may be determined based on the difference between the flow rate target, $Q_{TARGET,N}$, and the measured real time flow rate, $Q_{MEASURED,N}$, at one or more time points during the inhalation of subject 12. $Q_{e,N}$ can then be used to correct for errors in flow during an inspiration. The flow error may be acted upon using some method of control to correct for errors in real time patient flow. By way of a non-limiting example, the flow error could be acted upon by a servo control mechanism to correct the patient flow either directly or indirectly by adjusting one or more airway parameters.

Airway parameter module 48 is configured to determine one or more airway parameters of the airway of subject 12. In some embodiments, one or more of the one or more airway parameters may be determined once per inhalation. In some embodiments, one or more of the one or more airway parameters may be determined multiple times per inhalation of subject 12. One or more of the one or more airway parameters may be determined at regular time intervals (e.g., 10 ms) during an inhalation of subject 12. The one or more airway parameters may be determined one or more times for each individual inhalation in a series of inhalations. The information determined by airway parameter module 48 may be used for controlling pressure generator 14, stored in electronic storage 24, and/or used for other uses. The one or more airway parameters may comprise airway elastance parameter, E, airway resistance parameter, R, and/or other airway parameters. Airway parameter module 48 is configured such that a default value, $E_{START}$, of airway elastance parameter is used initially. This value may be corrected once per breath using input from the gas parameter module 42, using a servo mechanism, for example. The input to this servo mechanism may be one or more airway parameters. For example, the servo mechanism may act upon the total inspired volume error, $V_e$, to produce a new starting elastance parameter for the next inspiration. During a breath, the elastance parameter may also be adjusted in real time to account for errors in volume delivery, using another servo mechanism, where the input may be the flow error discussed previously, $Q_{e,N}$. Adjusting the elastance parameter value multiple times during the current inhalation of subject 12 can help compensate for large errors in real time flow rate.

The elastance parameter determined by airway parameter module 48 may be bounded by an upper bound and/or a lower bound. The elastance parameter may therefore reduce to the lower bound during the elastance parameter adjustments. Once at the lower bound, any additional flow error will not be immediately compensated for, allowing for the subject 12 to receive volume beyond that prescribed on the user interface 22, as the subject's muscle effort allows. During this period, pressure generator 14 will continue to provide pressure support to the subject 12. Although the real time adjusted elastance parameter may be adjusted down to a real time lower bound, the starting elastance parameter may not be less than a starting elastance parameter lower bound, which should be higher than the real time adjusted elastance parameter's lower bound. The starting elastance parameter lower bound may be greater than zero to aid in preventing hypoinflation. The lower bound on the starting elastance parameter provides a minimum non-zero starting point for system 10 if the patient ceases or greatly relaxes muscle effort. The boundary levels may be set by a user via user interface 22, programmed into system 10 at manufacture, and/or determined by other methods.

Airway parameter module 48 is configured such that airway resistance parameter, R, is determined based on the difference between the target peak flow (peak of $Q_{TARGET,N}$) and the measured peak flow (peak of $Q_{MEASURED,N}$), where the measured peak flow may be that received by the subject 12. A servo mechanism may act upon the error in peak flow to correct the airway resistance parameter. While it is not necessary to adjust the airway resistance parameter to maintain volume control, breath to breath adjustment is useful to maintain a prescribed flow pattern shape.

Minimum, maximum, and/or other bounds on the determined airway resistance parameter may be set such that R is bound to reasonable physiological values.

As described above related to gas parameter module 42 and airway parameter module 48, one or more parameters may be calculated based on other determined parameters. One or more parameters may be determined breath to breath (e.g., once per breath, once per inhalation). One or more parameters may be determined multiple times during a single inhalation. In some embodiments, one or more of the one or more gas parameters and/or the one or more airway parameters may be termed inner loop parameters, and/or outer loop parameters. Inner loop parameters may include those parameters determined multiple times during the inhalation of subject 12, and/or at other times. For example, the adjusted elastance parameter may be referred to as inner loop elastance, $E_{inner\ loop}$. Outer loop parameters may be determined based on the immediately previous inhalation by subject 12. The outer loop parameters may be determined once per breath, and/or at other times. The outer loop parameters may include, for example, $V_{SET}$, R, $E_{START}$, and/or other parameters.

Inspiratory pressure module 54 is configured to dynamically determine and/or adjust an inspiratory pressure level of the pressurized flow of breathable gas of the volume control mode therapy regime during an inhalation. The inspiratory pressure is dynamically determined and/or adjusted such that the target tidal volume and/or flow is achieved. The adjustment is based on the determined one or more gas parameters, the determined one or more airway parameters, and/or other information. The inspiratory pressure level is adjusted such that the inspiratory pressure level during an inhalation is not reduced to impede respiratory effort by subject 12 when the inhaled tidal volume exceeds the target tidal volume. During conventional volume control mode pressure support therapy the pressure provided to a patient during inhalation may be reduced responsive to respiratory effort by subject 12 preventing subject 12 from receiving volume above that prescribed.

In some embodiments, inspiratory pressure module 54 is configured to adjust the inspiratory pressure level based on one or more of gas parameters determined during one or more previous inhalations by the subject, airway parameters determined during one or more previous inhalations by the subject, and/or other information.

In some embodiments, inspiratory pressure module 54 is configured to adjust the inspiratory pressure level during the inhalation of subject 12 based on an airway model. In some embodiments, the model may be used to predict the actual flow rate based on the controlled pressure. As a general example, the model can be: Flow=A*pressure+B*pressure^2, wherein A and B are model parameters. When a particular flow target that relates to the target volume is desired within a breath, the model may be solved for pressure and pressure may be controlled based on set flow. If the measured flow deviates from the set flow, A and/or B may be updated in real time until the actual flow reaches the desired flow. The A and B parameters that produce the desired flow results continue to be used until the flow rate deviates from the set point. When the flow rate deviates from the set point, the system is configured "relearn" the best values for A and/or B, and adjusts the values for A and/or B accordingly. This allows starting the next breath with the best possible (previously adjusted) model parameters while also correcting the flow during the current breath. The end result resembles a traditional flow controller, but without issues related to controlling flow and/or letting pressure go unrestrained. The result is superior to that achieved by simple AVAPS, iVAPS, PRVC, and/or AutoFlow that target an inspiratory pressure and adjust the pressure breath by breath to achieve a volume, with the safety and comfort of pressure control.

In some embodiments, the airway model comprises a real time pressure set point algorithm configured to output a real time pressure set point level. The airway model may be utilized by inspiratory pressure module 54 to generate multiple real time pressure set point levels during the inhalation. Input variables to the airway model may include one or more gas parameters determined by the gas parameter module, one or more airway parameters determined by the airway parameter module, and/or other information. In some embodiments, inspiratory pressure module 54 is configured to adjust the inspiratory pressure level based on the proportional assist ventilation (PAV) equation. One or more of the one or more determined gas parameters, one or more of the determined airway parameters, and/or other parameters may comprise inputs to the proportional assist ventilation equation. The PAV equation is shown below.

$$P_N = RQ_N + E_N V_N$$

As described above, the real time flow set point, $Q_N$, the adjusted airway elastance parameter, $E_N$, and the real time volume set point, $V_N$, are determined multiple times per inhalation of subject 12. The airway resistance parameter, R, is determined once per breath. Inspiratory pressure module 54 is configured to generate multiple real time pressure set points, $P_N$, per inhalation of subject 12. Inspiratory pressure module 54 is configured to adjust the inspiratory pressure level of the pressurized flow of breathable gas based on the determined real time pressure set points.

In some embodiments, in a therapy regime that includes EPAP, EPAP may be unchanged by inspiratory pressure module 54, and/or system 10. After inhalation, the PAV model is no longer used to generate the individual pressure set points.

In some embodiments, the airway elastance parameter lower-bound described above may be zero. Therefore, the adjusted airway elastance parameter may reduce to zero during the inhalation of subject 12. When the adjusted airway elastance parameter is adjusted to zero, the instantaneous pressure set point is proportional to the flow set point as describe by the PAV equation, $P_N = RQ_N + 0$. When this condition occurs, the slope of the pressure set point becomes that of the flow set point. In this case, which may occur when subject 12 exerts large inspiratory effort, the pressure falls only to the flow set point profile scaled by R. To prevent hyperinflation of subject 12, an upper bound may be placed on the total inspired volume. User interface 22 is configured to provide an interface between system 10 and subject 12 and/or other users through which subject 12 and/or other users may provide information to and receive information from system 10.

User interface 22 is configured to receive entry and/or selection of control inputs from subject 12 and/or other users that select a target tidal volume. Other users may comprise a caregiver, a doctor, a decision maker, and/or other users. This enables data, cues, results, and/or instructions and any other communicable items, collectively referred to as "information," to be communicated between a user (e.g., subject 12) and one or more of pressure generator 14, processor 20, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Figure 2:
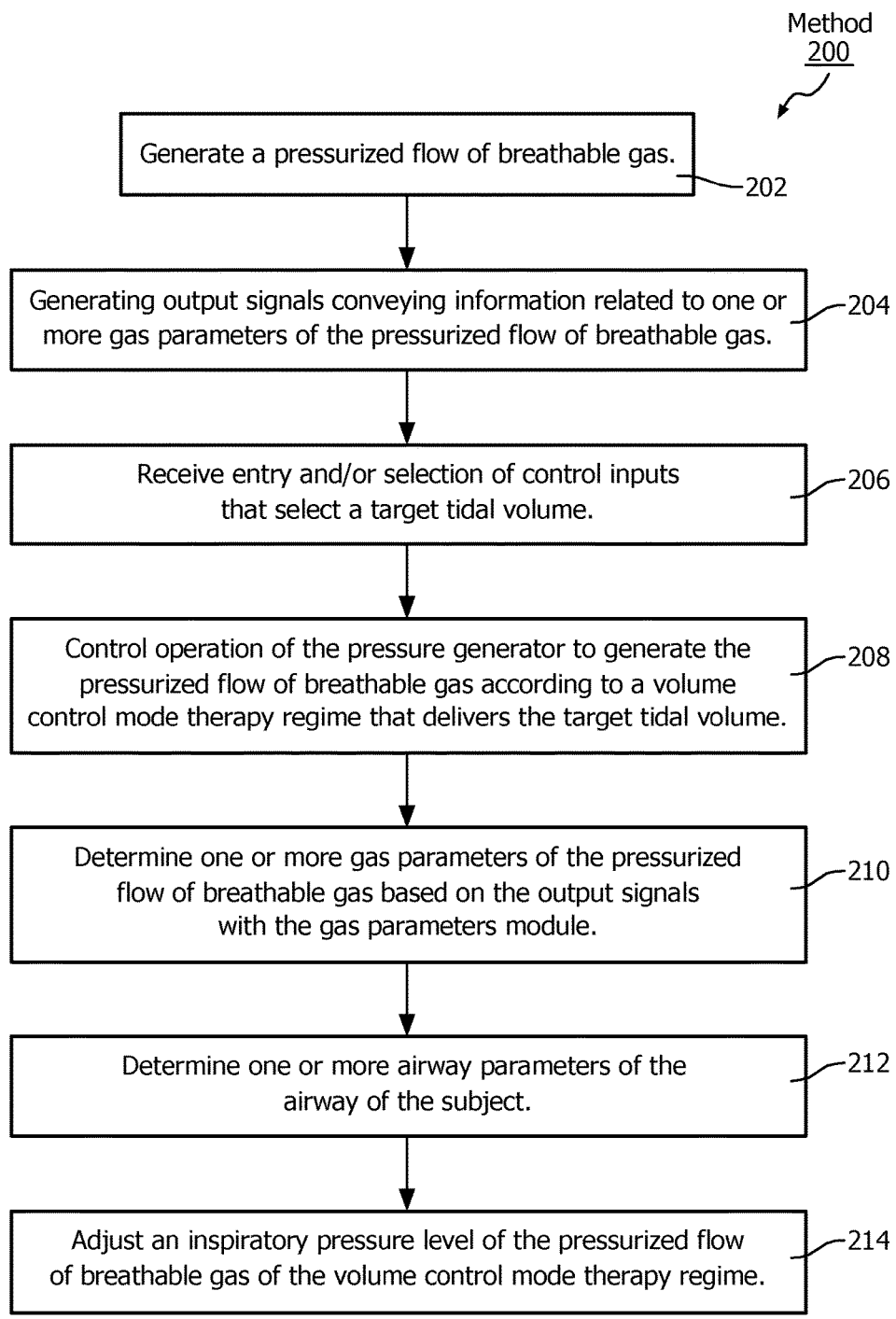
FIG. 2 illustrates a method to deliver a pressurized flow of breathable gas to the airway of a subject with a mechanical ventilator system.

FIG. 2 illustrates a method 200 to deliver a pressurized flow of breathable gas to the airway of a subject with a mechanical ventilator system. The mechanical ventilator system comprising a pressure generator, one or more sensors, a user interface, and one or more processors, the one or more processors configured to execute computer program modules, the computer program modules comprising a control module, a gas parameter module, an airway parameter module, and an inspiratory pressure module. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, the pressurized flow of breathable gas is generated. In some embodiments, operation 202 is performed by a pressure generator the same as or similar to pressure generator 14 (shown in FIG. 1 and described herein).

At an operation 204, output signals conveying information related to one or more gas parameters of the pressurized flow of breathable gas are generated. In some embodiments, operation 204 is performed by sensors the same as or similar to sensors 18 (shown in FIG. 1 and described herein).

At an operation 206, entry and/or selection of control inputs that select a target tidal volume are received. In some embodiments, operation 206 is performed by a user interface the same as or similar to user interface 22 (shown in FIG. 1 and described herein).

At an operation 208, operation of the pressure generator is controlled to generate the pressurized flow of breathable gas according to a volume control mode therapy regime that delivers the target tidal volume. In some embodiments, operation 208 is performed by a computer program module the same as or similar to control module 40 (shown in FIG. 1 and described herein).

At an operation 210, one or more gas parameters of the pressurized flow of breathable gas are determined. The one or more gas parameters are determined based on the output signals. The one or more gas parameters are determined multiple times per inhalation of the subject. The one or more gas parameters may comprise a real time flow rate set point, a real time volume set point, and/or other gas parameters. In some embodiments, operation 210 is performed by a computer program module the same as or similar to gas parameter module 42 (shown in FIG. 1 and described herein).

At an operation 212, one or more airway parameters of the airway of the subject are determined. The one or more airway parameters are determined multiple times per inhalation of the subject. The one or more airway parameters may comprise airway elastance parameter, airway resistance parameter, and/or other airway parameters. In some embodiments, operation 212 is performed by a computer program module the same as or similar to airway parameter module 48 (shown in FIG. 1 and described herein).

At an operation 214, an inspiratory pressure level of the pressurized flow of breathable gas of the volume control therapy regime is determined and/or adjusted. The pressure level is determined and/or adjusted based on the determined one or more airway parameters. In some embodiments, the inspiratory pressure level is adjusted based on one or more of gas parameters determined during one or more previous inhalations by the subject, or airway parameters determined during one or more previous inhalations by the subject. In some embodiments, the inspiratory pressure level is adjusted based on the proportional assist ventilation equation, and wherein one or more of the one or more determined gas parameters, one or more of the determined airway parameters, and/or other parameters comprise inputs to the proportional assist ventilation equation. The pressure level is adjusted such that the inspiratory pressure level during an inhalation is not reduced to impede respiratory effort by the subject responsive to the target tidal volume being exceeded during the inhalation. In some embodiments, operation 214 is performed by a computer program module the same as or similar to inspiratory pressure module 54 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A mechanical ventilator system configured to deliver a pressurized flow of breathable gas to the airway of a subject, the mechanical ventilator system comprising:
   a pressure generator configured to generate the pressurized flow of breathable gas;
   one or more sensors configured to generate output signals conveying information related to one or more gas parameters of the pressurized flow of breathable gas;
   a user interface configured to receive entry and/or selection of control inputs that select a target tidal volume; and
   one or more processors configured to execute computer program modules, the computer program modules comprising:
      a control module configured to control operation of the pressure generator to generate the pressurized flow of breathable gas according to a volume control mode therapy regime that delivers the target tidal volume;
      a gas parameter module configured to determine one or more gas parameters of the pressurized flow of breathable gas based on the output signals, wherein the one or more gas parameters are determined multiple times per inhalation of the subject;
      an airway parameter module configured to determine one or more airway parameters of the airway of the subject, wherein the one or more airway parameters are determined multiple times per inhalation of the subject; and
      an inspiratory pressure module configured to:
         (1) dynamically determine an inspiratory pressure level of the pressurized flow of breathable gas of the volume control mode therapy regime during an inhalation to achieve the target tidal volume, the determination based on the determined one or more airway parameters and the determined one or more gas parameters;
         (2) determine whether the target tidal volume is exceeded during the inhalation; and
         (3) maintain, responsive to the target tidal volume being exceeded during the inhalation, the inspiratory pressure level during the inhalation so the inspiratory pressure level is not reduced to impede respiratory effort by the subject by adjusting the inspiratory pressure level based on inner loop parameters and outer loop parameters, wherein the inner loop parameters comprise one or more of gas parameters determined multiple times during the inhalation by the subject, or airway parameters determined multiple times during the s inhalation by the subject, and wherein the outer loop parameters comprise one or more of gas parameters determined based on an immediately previous inhalation by the subject, or airway parameters determined based on the immediately previous inhalation by the subject.

2. The system of claim 1, wherein the one or more airway parameters comprise airway elastance parameter and airway resistance parameter.

3. The system of claim 1, wherein the one or more gas parameters comprise a real time flow rate set point and a real time volume set point.

4. The system of claim 1, wherein the inspiratory pressure module is configured to determine the inspiratory pressure level dynamically during the inhalation based on an airway model, the model based on the one or more airway parameters, the model configured to return the inspiratory pressure level as a function of one or more of the one or more gas parameters such that a target tidal flow rate is achieved during the inhalation.

5. A method to deliver a pressurized flow of breathable gas to the airway of a subject with a mechanical ventilator system, the mechanical ventilator system comprising a pressure generator, one or more sensors, a user interface, and one or more processors, the one or more processors configured to execute computer program modules, the computer program modules comprising a control module, a gas parameter module, an airway parameter module, and an inspiratory pressure module, the method comprising:
   generating the pressurized flow of breathable gas with the pressure generator;
   generating output signals conveying information related to one or more gas parameters of the pressurized flow of breathable gas with the one or more sensors;
   receiving entry and/or selection of control inputs that select a target tidal volume with the user interface;
   controlling operation of the pressure generator to generate the pressurized flow of breathable gas according to a volume control mode therapy regime that delivers the target tidal volume with the control module;
   determining one or more gas parameters of the pressurized flow of breathable gas based on the output signals with the gas parameter module, wherein the one or more gas parameters are determined multiple times per inhalation of the subject;
   determining one or more airway parameters of the airway of the subject with the airway parameter module, wherein the one or more airway parameters are determined multiple times per inhalation of the subject; and
   dynamically determining an inspiratory pressure level of the pressurized flow of breathable gas of the volume control mode therapy regime during an inhalation to achieve the target tidal volume, with the inspiratory pressure module, the determination based on the determined one or more airway parameters and the determined one or more gas parameters;
   determining, with the inspiratory pressure module, whether the target tidal volume is exceeded during the inhalation; and
   maintaining with the inspiratory pressure module, responsive to the target tidal volume being exceeded during the inhalation, the inspiratory pressure level during the inhalation so the inspiratory pressure level is not reduced to impede respiratory effort by the subject, wherein maintaining comprises adjusting the inspiratory pressure level with the inspiratory pressure module based on inner loop parameters and outer loop parameters, wherein the inner loop parameters comprise one or more of gas parameters determined multiple times during the inhalation by the subject, or airway parameters determined multiple times during the inhalation by the subject, and wherein the outer loop parameters comprise one or more of gas parameters determined based on an immediately previous inhalation by the subject, or airway parameters determined based on the immediately previous inhalation by the subject.

6. The method of claim 5, wherein the one or more airway parameters comprise airway elastance parameter and airway resistance parameter.

7. The method of claim 5, wherein the one or more gas parameters comprise a real time flow rate set point and a real time volume set point.

8. The method of claim 5, further comprising determining the inspiratory pressure level dynamically during the inhalation with the inspiratory pressure module based on an airway model, the model based on the one or more airway parameters, the model configured to return the inspiratory pressure level as a function of one or more of the one or more gas parameters such that a target tidal flow rate is achieved during the inhalation.

9. A mechanical ventilator system configured to deliver a pressurized flow of breathable gas to the airway of a subject, the mechanical ventilator system comprising:
    means for generating the pressurized flow of breathable gas;
    means for generating output signals conveying information related to one or more gas parameters of the pressurized flow of breathable gas;
    means for receiving entry and/or selection of control inputs that select a target tidal volume; and
    means for executing computer program modules, the computer program modules comprising:
        means for controlling operation of the means for generating the pressurized flow of breathable gas to generate the pressurized flow of breathable gas according to a volume control mode therapy regime that delivers the target tidal volume;
        means for determining one or more gas parameters of the pressurized flow of breathable gas based on the output signals, wherein the one or more gas parameters are determined multiple times per inhalation of the subject;
        means for determining one or more airway parameters of the airway of the subject, wherein the one or more airway parameters are determined multiple times per inhalation of the subject;
        means for dynamically determining an inspiratory pressure level of the pressurized flow of breathable gas of the volume control mode therapy regime during an inhalation to achieve the target tidal volume, the determination based on the determined one or more airway parameters and the determined one or more gas parameters;
        means for determining whether the target tidal volume is exceeded during the inhalation; and
        means for maintaining, responsive to the target tidal volume being exceeded during the inhalation, the inspiratory pressure level during the inhalation so the inspiratory pressure level is not reduced to impede respiratory effort by the subject by adjusting the inspiratory pressure level based on inner loop parameters and outer loop parameters, wherein the inner loop parameters comprise one or more of gas parameters determined multiple times during the inhalation by the subject, or airway parameters determined multiple times during the inhalation by the subject, and wherein the outer loop parameters comprise one or more of gas parameters determined based on an immediately previous inhalation by the subject, or airway parameters determined based on the immediately previous inhalation by the subject.

10. The system of claim 9, wherein the one or more airway parameters comprise airway elastance parameter and airway resistance parameter.

11. The system of claim 9, wherein the one or more gas parameters comprise a real time flow rate set point and a real time volume set point.

12. The system of claim 9, wherein the means for dynamically determining is configured to determine the inspiratory pressure level dynamically during the inhalation based on an airway model, the model based on the one or more airway parameters, the model configured to return the inspiratory pressure level as a function of one or more of the one or more gas parameters such that a target tidal flow rate is achieved during the inhalation.

* * * * *